United States Patent
Slatter et al.

(10) Patent No.: US 7,291,648 B2
(45) Date of Patent: **\*Nov. 6, 2007**

(54) 3,3-DIPHENYLPROPYLAMINES USEFUL IN THERAPY

(75) Inventors: John Gregory Slatter, Bellevue, WA (US); Raymond Charles Grabiak, Maryland Heights, MO (US); Robert John Kaufman, University City, MO (US)

(73) Assignee: Pfizer Inc., New York, NY (US)

( * ) Notice: Subject to any disclaimer, the term of this patent is extended or adjusted under 35 U.S.C. 154(b) by 147 days.

This patent is subject to a terminal disclaimer.

(21) Appl. No.: 11/466,814

(22) Filed: Aug. 24, 2006

(65) Prior Publication Data

US 2006/0281812 A1    Dec. 14, 2006

Related U.S. Application Data

(60) Division of application No. 11/212,330, filed on Aug. 25, 2005, now Pat. No. 7,119,121, which is a continuation of application No. 10/832,555, filed on Apr. 26, 2004, now abandoned.

(60) Provisional application No. 60/465,372, filed on Apr. 25, 2003.

(51) Int. Cl.
*A61K 31/13* (2006.01)
*C07C 211/00* (2006.01)

(52) U.S. Cl. .................. 514/648; 564/315; 564/316

(58) Field of Classification Search ................ 514/648; 564/315, 316

See application file for complete search history.

(56) References Cited

U.S. PATENT DOCUMENTS 7,119,121 B2 * 10/2006 Slatter et al. ............... 514/648

FOREIGN PATENT DOCUMENTS

| WO | WO 9411337 | 5/1994 |
| WO | WO 8906644 | 7/1998 |
| WO | WO 9958478 | 11/1999 |
| WO | WO 03035599 | 5/2003 |

OTHER PUBLICATIONS

Nilvebrant, et al., "Tolterodine-a new bladder selective antimuscarinice agent"; European Journal of Pharmacology; 327, (1997) pp. 195-207.

* cited by examiner

*Primary Examiner*—Samuel Bartts
(74) *Attorney, Agent, or Firm*—Gregg C. Benson; Carl J. Goddard

(57) ABSTRACT

Novel 3,3-diphenylpropylamines of the formula

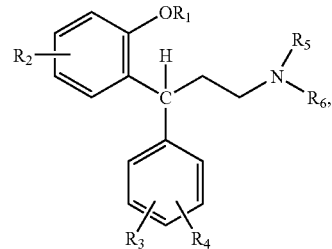

and stereoisomers and physiologically acceptable acid addition salt thereof; wherein $R_1$, $R_2$, $R_3$, $R_4$, $R_5$, and $R_6$ are as defined herein; methods of use thereof; and pharmaceutical compositions thereof.

5 Claims, No Drawings

3,3-DIPHENYLPROPYLAMINES USEFUL IN THERAPY

PRIORITY CLAIM

This application is a divisional of U.S. application Ser. No. 11/212,330, filed Aug. 25, 2005, now U.S. Pat No. 7,119,121, which is a continuation of U.S. application Ser. No. 10/832,555, filed Apr. 26, 2004,now abandoned, which claims priority to U.S. Provisional Application Ser. No. 60/465,372, filed Apr. 25, 2003.

TECHNICAL FIELD

The present invention relates to novel therapeutic compounds, pharmaceutical compositions containing the same, the compounds for use as medicaments, and use of the compounds for the manufacture of specific medicaments. The present invention also concerns a method of treatment involving administration of the compounds.

The novel compounds are useful as antimuscarinic agents. In particular, the novel compounds are useful for the treatment or control of events mediated by acetylcholine, such as urinary disorders.

BACKGROUND OF THE INVENTION

U.S. Pat. No. 5,382,600 discloses (substituted) 3,3-diphenylpropylamines useful for treating urinary incontinence. In particular, it discloses 2-[(1R)-3-(diisopropylamino)-1-phenylpropyl)-4-methylphenol, also known as N,N-diisopropyl-3-(2-hydroxy-5-methylphenyl)-3-phenylpropylamine, with the generic name of tolterodine, as being useful to treat urinary incontinence. Tolterodine is the compound of Example 22 of U.S. Pat. No. 5,382,600.

It is preferred that tolterodine is prepared by the processes of International Publication WO98/29402 (U.S. Pat. No. 5,922,914).

U.S. Pat. No. 5,559,269 and U.S. Pat. No. 5,686,464 disclose hydroxytolterodine and related compounds as being useful to treat urinary incontinence. Hydroxytolterodine is also the major metabolite of tolterodine (Nilvebrant et al, 1997, Eur J Pharmacol, 327:195-207).

The presence of an additional hydroxyl group in tolterodine increases its hydrophilic property. In an attempt to avoid this increase, WO 99/58478 discloses substituted 3,3-diphenylpropylamines for use as pharmaceutically active substances.

The international patent application WO 98/43942 discloses therapeutically active diarylpropylamines, which have favorable anticholinergic properties, and which can be used for the treatment of disorders related to urinary incontinence.

Gillberg et al, Eur J Pharmacol 349(2-3): 285-292 (1998) have suggested that decreased potency for a muscarinic antagonist at the m3 receptor may improve the ratio of desired effects at the bladder, relative to effects on the salivary glands that result in dry mouth. Thus, a selectivity for muscarinic M3/m3 over M2/m2 receptors may result in a more pronounced effect on salivation than on bladder contraction.

It has been observed that metabolism of 3,3-diphenylpropylamines occurs in vivo. This well-known phenomenon may be involved in increased drug clearance, diminished bioavailability, diminished half-life in vivo, drug interactions, and pharmacokinetic differences between subjects, depending on their drug metabolizing enzyme activities.

Postlind et al, Drug Metabolism and Disposition, 26(4): 289-293 (1993) disclose that tolterodine is metabolized by various cytochrome P450 enzymes. The two main metabolic events are oxidation of the 5-methyl group, catalyzed by the CYP2D6 enzyme, and dealkylation of the nitrogen, catalyzed by the CYP3A enzyme.

Thus, despite the above advances in the art, it is desirable to develop novel 3,3-diphenylpropylamines that are less prone to metabolism in vivo.

SUMMARY OF THE INVENTION

For these and other purposes, it is an object of the present invention to provide novel 3,3-diphenylpropylamines having different affinity profiles for muscarinic receptors.

It is also an object of the present invention to provide novel 3,3-diphenylpropylamines with antimuscarinic activity that helps avoid side effects in a treated subject from the medication.

According to another aspect, it is an object of the present invention to provide novel 3,3-diphenylpropylamines, which are not readily metabolized in vivo.

It is another object of the present invention to provide novel 3,3-diphenylpropylamines, which have a low clearance.

It is also an object of the present invention to provide novel 3,3-diphenylpropylamines, which have a beneficial bioavailability.

It is another object of the present invention to provide novel 3,3-diphenylpropylamines, which have a long half-life in vivo.

It is also an object of the present invention to provide novel 3,3-diphenylpropylamines, which possess a suitable drug interaction profile.

It is yet another object of the present invention to provide novel 3,3-diphenylpropylamines, which provide small pharmacokinetic differences between poor and extensive metabolizers.

Finally, it is an object of the present invention to provide novel 3,3-diphenylpropylamines, which provide low inter-subject variability in pharmacokinetics and pharmacodynamics.

For these and other objects that will be evident from the following disclosure, the present invention provides according to a first aspect a 3,3-diphenylpropylamine of the formula

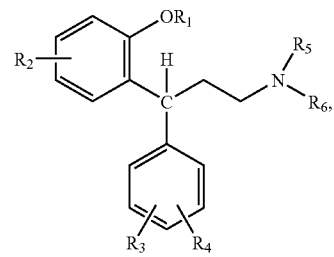

and any stereoisomers thereof;

wherein $R_1$ represents

—H or —$CH_3$;

$R_2$ represents —$CX_3$, —$CR_{2-1}X_2$, —$CR_{2-1}R_{2-2}X$, or —$CR_{2-1}R_{2-2}H$, wherein X represents halogen, and $R_{2-1}$ and $R_{2-2}$ independently represent —H or —($C_1$-$C_4$ alkyl), optionally substituted with halogen;

$R_3$ and $R_4$ independently represent —H, —$OCH_3$, —OH, —$CONH_2$, —$SO_2NH_2$, —F, —Cl, —Br, —I, —$CF_3$, or —($C_1$-$C_4$ alkyl), optionally substituted with one or two —OH, —($C_1$-$C_4$ alkoxy) —COOH, or —CO—O—($C_1$-$C_3$ alkyl); and $R_5$ and $R_6$ independently represent $C_1$-$C_6$ alkyl, optionally substituted with hydroxyl, wherein $R_5$ and $R_6$ together contain at least three carbon atoms, and wherein $R_5$ and $R_6$ may form a ring together with the amine nitrogen;

provided that $R_2$ comprises at least one halogen;

or a physiologically acceptable acid addition salt thereof.

Moreover, the present invention provides a pharmaceutical composition comprising a therapeutically effective amount of a 3,3-diphenylpropylamine according to the invention, and a suitable pharmaceutical carrier therefor.

The present invention also provides a 3,3-diphenylpropylamine according to the invention for use as a medicament. In particular, the present invention provides novel use of a 3,3-diphenylpropylamine according to the invention for the manufacture of a medicament for treating urinary disorders.

Finally, the present invention also provides a method of treating urinary disorders in a mammal, including man, comprising administering to said mammal, in need of such a treatment, a therapeutically effective amount of a 3,3-diphenylpropylamine according to the invention.

DETAILED DESCRIPTION OF THE INVENTION

The present invention provides a 3,3-diphenylpropylamine of the formula

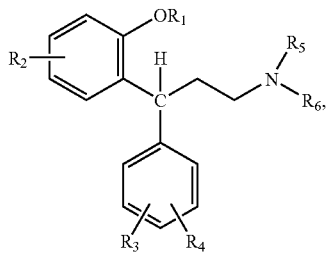

and any stereoisomers thereof. The invention also provides physiologically acceptable acid addition salts thereof.

In the formula above, $R_1$ may represent —H or —$CH_3$. In one embodiment of the 3,3-diphenylpropylamine according to the invention, $R_1$ represents hydrogen.

$R_2$ represents —$CX_3$, —$CR_{2-1}X_2$, —$CR_{2-1}R_{2-2}X$, or —$CR_{2-1}R_{2-2}H$, wherein X represents halogen, and $R_{2-1}$ and $R_{2-2}$ independently represent —H or —($C_1$-$C_4$ alkyl), optionally substituted with halogen. $R_2$ must comprise at least one halogen. Preferably, $R_2$ represents —$CX_3$, —$CR_{2-1}X_2$ or —$CR_{2-1}R_{2-2}X$.

In an embodiment of the 3,3-diphenylpropylamine according to the invention, the $R_2$ group is situated opposite (para) to the $OR_1$ group in their common phenyl ring structure. In a particular embodiment, $R_2$ represents —$CX_3$. In specific embodiments of the $R_2$ group, X represents fluorine.

In a specific embodiment, $R_2$ represents —$CF_3$. Without being bound to any particular theory, it is contemplated that the bond strength of the C—F bond, relative to that of a C—H bond, can decrease or preclude metabolism by cytochrome P450 enzymes. This may be optimal for safety and lack of CYP2D6 metabolism. Without being bound to any particular theory, it is also contemplated that the —$CF_3$ group provides increased lipophilicity and, when —$OR_1$ represents —OH (i.e. $R_1$ represents hydrogen), provides inductive effects on the acidity of that —OH group, that may impart favorable conformational changes to the molecule.

The substituents $R_3$ and $R_4$ may be the same or different. $R_3$ and $R_4$ independently represent —H, —$OCH_3$, —OH, —$CONH_2$, —$SO_2NH_2$, —F, —Cl, —Br, —I, —$CF_3$, or —($C_1$-$C_4$ alkyl), optionally substituted with one or two —OH, —($C_1$-$C_4$ alkoxy), —COOH, or —CO—O—($C_1$-$C_3$ alkyl).

In an embodiment of the 3,3-diphenylpropylamine according to the invention, at least one of $R_3$ and $R_4$ represents —H. In a particular embodiment, both $R_3$ and $R_4$ represent —H.

The substituents $R_5$ and $R_6$ may be the same or different. $R_5$ and $R_6$ independently represent $C_1$-$C_6$ alkyl, optionally substituted with hydroxyl, wherein $R_5$ and $R_6$ together contain at least three carbon atoms, and wherein $R_5$ and $R_6$ may form a ring together with the amine nitrogen.

In one embodiment of the 3,3-diphenylpropylamine according to the invention, at least one of $R_5$ and $R_6$ represents $C_1$-$C_3$ alkyl. In a particular embodiment, the $C_1$-$C_3$ alkyl is isopropyl. In a specific embodiment, both $R_5$ and $R_6$ represent isopropyl.

In an embodiment of the 3,3-diphenylpropylamine according to the invention, the carbon stereocenter is (R). In another embodiment of the 3,3-diphenylpropylamine according to the invention, the carbon stereocenter is (S). In yet another embodiment of the 3,3-diphenylpropylamine according to the invention, it is present in the form of a mixture of stereoisomers.

Particular embodiments of the 3,3-diphenylpropylamines according to the invention comprise the group consisting of:

N,N-diisopropyl-3-(2-methoxy-5-trifluoromethylphenyl)-3-phenylpropanamine;

N,N-diisopropyl-3-(2-hydroxy-5-trifluoromethylphenyl)-3-phenylpropanamine; and

N,N-diisopropyl-3-(2-hydroxy-5-trifluoromethylphenyl)-3-phenylpropanamine tartrate.

In a particular embodiment of the invention, the 3,3-diphenylpropylamine is N,N-diisopropyl-3-(2-hydroxy-5-trifluoromethylphenyl)-3-phenylpropanamine. As described in the following examples, this compound exhibits favorable binding properties with regard to muscarinic receptors m1-m4. In particular, it can be expected that certain side effects resulting from the use of muscarinic antagonists are avoided or lessened to some extent by employing the 3,3-diphenylpropylamines according to the invention.

It is also contemplated that N,N-diisopropyl-3-(2-hydroxy-5-trifluoromethylphenyl)-3-phenylpropanamine, as well as other compounds according to the invention, can avoid being metabolized by the CYP2D6 enzyme. This is advantageous since metabolism by this enzyme accounts for a substantial part of the intersubject variability in the pharmacokinetic properties of tolterodine. CYP2D6 is a polymorphic enzyme, with about 10% of the population being genetically "poor metabolizers". Therefore, compounds according to the invention may be helpful in providing a medicament that avoids the costs and problems related to intersubject variability in pharmacokinetics.

The novel class of compounds according to the present invention are antimuscarinic agents. "Antimuscarinic agents" refer to muscarinic receptor antagonists. Examples of known antimuscarinic agents include tolterodine, hydroxytolterodine, 2-(diisopropylamino)ethyl-1-phenylcyclopentanecarboxylate, propiverine, oxybutynin, trospium, darifenacin, solifenacin, temiverine, ipratropium, and tiotropium.

The compounds of the invention are preferably administered as salts with a pharmaceutically acceptable acid. The preferred pharmaceutically acceptable salts, organic or inorganic, include salts of the following acids: tartaric, hydrochloric, hydrobromic, hydroiodic, sulfuric, phosphoric, nitric, citric, methanesulfonic, $CH_3—(CH_2)_n—COOH$ where n is 0 to 4, $HOOC—(CH_2)_n—COOH$ where n is 1 to 4, $HOOC—CH=CH—COOH$, and benzoic. For other acceptable salts, see Int. J. Pharm., 33, 201-217 (1986). A particularly preferred salt is tartrate.

According to another aspect of the invention, there is provided a pharmaceutical composition comprising a therapeutically effective amount of a 3,3-diphenylpropylamine according to the invention, and a suitable pharmaceutical carrier therefor.

The compounds according to the invention, in the form of free base or salts with pharmaceutically acceptable acids, or solutions thereof, can be brought into suitable dosage forms, such as compositions for administration through the oral, rectal, transdermal, parenteral, nasal, or pulmonary route in accordance with accepted pharmaceutical procedures. Such pharmaceutical compositions according to the invention comprise the compounds according to the invention in association with compatible pharmaceutically acceptable carrier materials, or diluents, as is well known in the art. The carriers may be any inert material, organic or inorganic, suitable for administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmaceutically active agents, and conventional additives such as stabilizers, wetting agents, emulsifiers, flavoring agents, buffers, binders, disintegrants, lubricants, glidants, antiadherents, propellants, and the like.

The novel compounds according to the present invention can be administered in any suitable way. The compounds according to the invention can be made up in solid or liquid form, such as tablets, capsules, powders, syrups, elixirs and the like, aerosols, sterile solutions, suspensions or emulsions, and the like.

The term "effective amount" refers to a therapeutically effective amount for treating urinary disorders. The terms "therapy" and "therapeutically" encompass all kinds of treatments, including prophylaxis. In particular, "therapeutically effective" means that it is effective for anti-cholinergic treatment.

The dosage of the specific compound according to the invention will vary depending on its potency, the mode of administration, the age and weight of the patient and the severity of the condition to be treated. For example, the medication may be administered orally once or twice daily, or less frequently, or intermittently.

The present invention also provides a 3,3-diphenylpropylamine according to the invention for use as a medicament. In particular, the present invention provides novel use of a 3,3-diphenylpropylamine according to the invention for the manufacture of a medicament for treating urinary disorders.

The compounds of the invention have anti-cholinergic properties. Thus, they are useful for the treatment of acetylcholine-mediated disorders. In particular, they are useful for treating urinary disorders.

"Urinary disorders" and symptoms thereof include some or all of the following: urgency, frequency, incontinence, urine leakage, enuresis, dysuria, hesitancy, and difficulty of emptying bladder. In particular, urinary disorders include urinary incontinence, caused by e.g. unstable or overactive urinary bladder.

Overactive urinary bladder encompasses variants of urinary disorders, including overactive detrusor (detrusor instability, detrusor hyperreflexia) and sensory urgency, as well as symptoms of detrusor overactivity, e.g. urge incontinence, urgency, urinary frequency, and LUTS (Lower Urinary Tract Symptoms), including obstructive urinary symptoms, such as slow urination, dribbling at the end of urination, inability to urinate and/or the need to strain to urinate at an acceptable rate, or irritating symptoms such as frequency, dry overactive bladder, and/or urgency).

Other conditions are also included, which give rise to urinary frequency, urgency and/or urge incontinence. Overactive bladder disorders also include nocturia and mixed incontinence. While overactive bladder is often associated with detrusor muscle instability, disorders of bladder function may also be due to neuropathy of the central nervous system (detrusor hyperreflexia), including spinal cord and brain lesions, such as multiple sclerosis and stroke. Overactive bladder symptoms may also result from, for example, male bladder outlet obstruction (usually due to prostatic hypertrophy), interstitial cystitis, local edema and irritation due to focal bladder cancer, radiation cystitis due to radiotherapy to the pelvis, and cystitis.

Finally, the present invention also provides a method of treating urinary disorders in a mammal, including man, comprising administering to said mammal, in need of such a treatment, a therapeutically effective amount of a 3,3-diphenylpropylamine according to the invention.

The compounds of the present invention are used to treat mammals, including man, cat, dog, and horse. It is preferred that the mammal is a human.

Without being limited thereto, the invention will now be further illustrated by way of examples.

EXAMPLES

The synthesis of a compound according to the invention will in the following be described in detail in examples 1-10. The synthesis scheme can be summarized as follows:

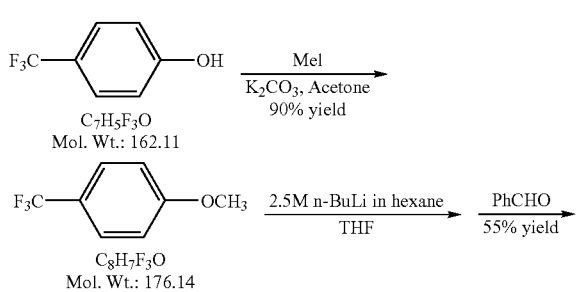

-continued

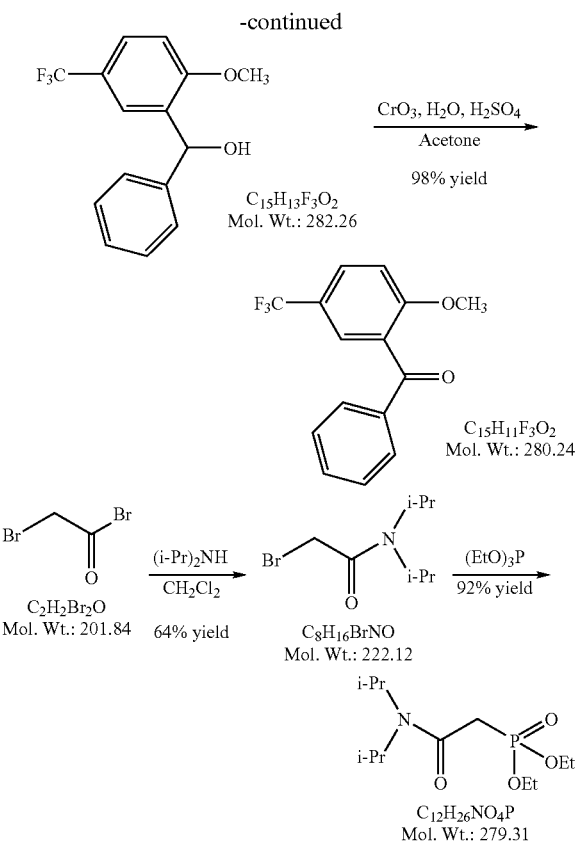

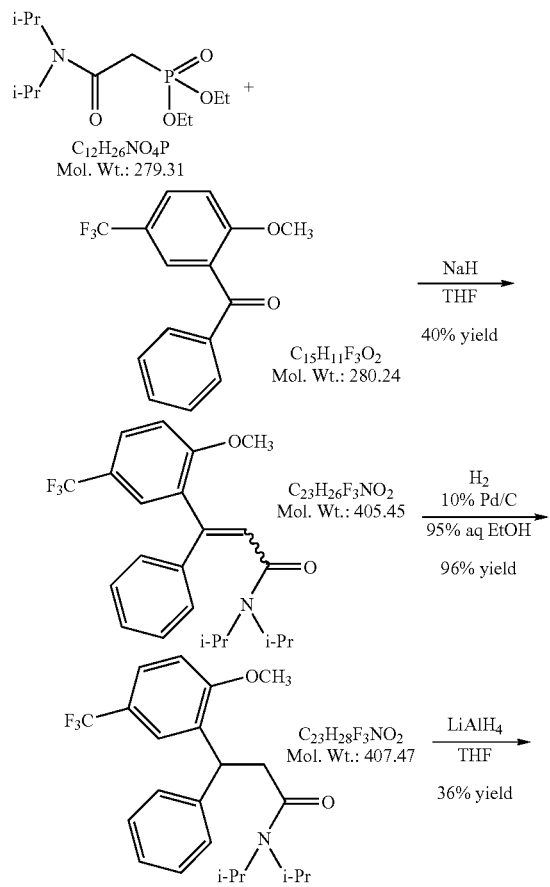

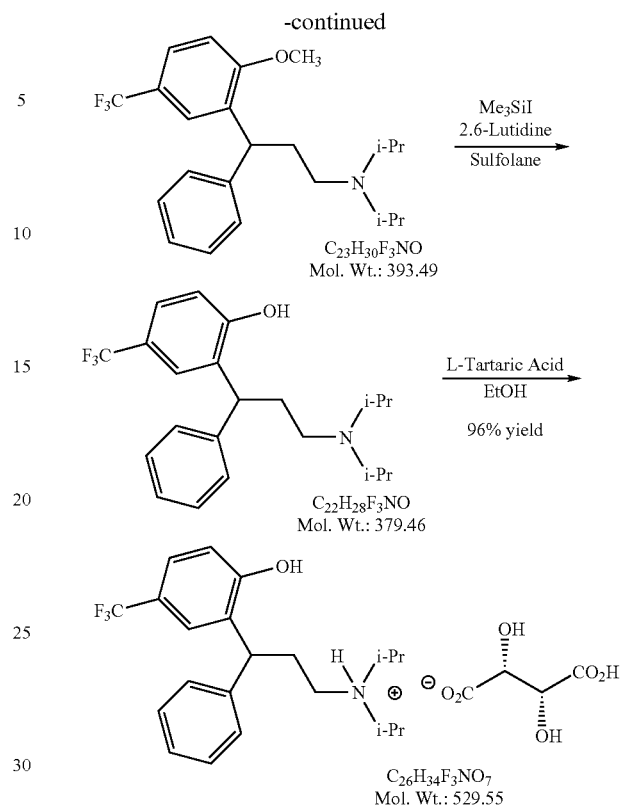

It is understood that these examples are merely illustrative and that variations of this concept can easily be achieved by the skilled man in the art.

Example 1

4-Trifluoromethylanisole

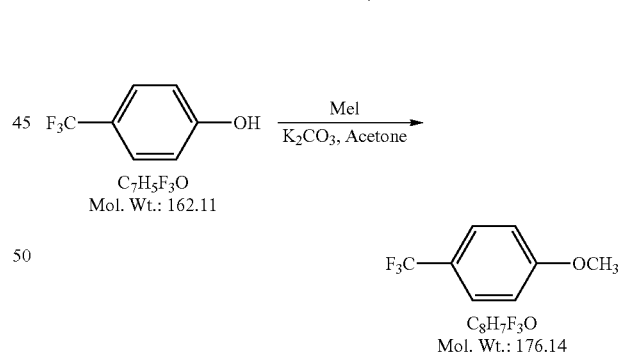

Under a nitrogen atmosphere, a mechanically stirred mixture of 4-trifluoromethylphenol (100.0 g; 0.617 mol, Aldrich), powdered potassium carbonate (87.7 g; 0.635 mol, Aldrich) and iodomethane (54.0 mL; 0.867 mol, Aldrich) in 1250 mL acetone was heated at reflux (5:04 pm) for a total of 8 h.

Gas chromatography (GC; a Hewlett Packard 5890 instrument) of an aliquot of the mother liquor showed product with no detectable starting phenol. The slurry was suction filtered and the light yellow solids were washed with acetone (200 mL). The light yellow filtrate was concentrated on a rotary evaporator at 25° C. to give a light yellow oily solid.

This material was partitioned between ether (1000 mL) and 10% aqueous NaOH (100 mL). The ether layer was dried over MgSO$_4$, filtered and washed with ether. The near colorless filtrate was concentrated on a rotary evaporator at 20-30° C. to give a pale yellow oil; 97.75 g. $^1$H-NMR and $^{13}$C-NMR were consistent with 4-trifluoromethylanisole. GC showed 99.5% of the desired product. The yield was 89.9%.

$^1$H-NMR (CDCl$_3$, ppm): 7.56 & 7.52 (Ar 2H); 6.97 & 6.95 (Ar 2H); 3.84 (OCH$_3$).

Example 2

(2-Methoxy-5-trifluoromethylphenyl)-phenyl methanol

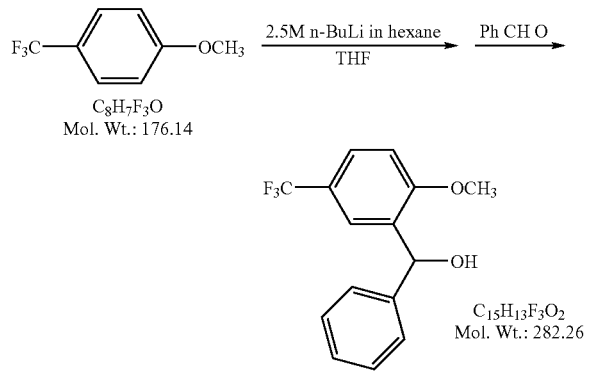

All glassware was dried in the oven at 105° C. overnight and assembled hot under nitrogen. Under a nitrogen atmosphere in a 4-neck, 3 L flask, a solution of 4-trifluoromethylanisole (97.75 g; 0.555 mol) in 1300 mL anhydrous tetrahydrofuran was stirred mechanically in a dry ice-acetone bath. A 2.5 M solution of n-Butyllithium in hexane (269 mL; 0.672 mol) was added dropwise at from −67° C. to −71° C. over a period of 56 min. The addition funnel was rinsed with anhydrous THF (2×50 mL).

After stirring in the dry ice-acetone bath for 32 min, this bath was replaced with an ice bath. The light orange solution was allowed to warm to 0° C. in the ice bath over a period of 97 min to give a dark amber solution. A solution of benzaldehyde (68.5 g; 0.646 mol, Aldrich) in 200 mL anhydrous THF was added dropwise at 0-10° C. (mainly 7-9° C.) over a period of 49 min. As the addition proceeded, the color of the reaction solution changed from the dark amber to a light orange. The addition funnel was rinsed with anhydrous THF (2×50 mL) and the ice bath was removed.

The light orange solution was stirred under nitrogen for 1 h as the temperature increased from 5.5° C. to 17.5° C. The light orange solution was cooled again in an ice bath. 20% Aqueous NH$_4$Cl (500 mL) was added dropwise at 7-11° C. over 13 min. The resulting mixture was extracted with ether (2000 mL). The ether extract was washed successively with water (1000 mL), 10% aqueous NaHCO$_3$ (1000 mL) and then saturated brine (1000 mL). The ether layer was dried over MgSO$_4$, filtered and concentrated on a rotary evaporator at 45° C. to give a light yellow oily solid; 160.65 g. GC showed a high boiling component along with some starting 4-trifluoromethylanisole and benzaldehyde. This oily solid was slurried in hexane (200 mL) and cooled in the refrigerator overnight.

The slurry was suction filtered and the light yellow solid was crushed with a spatula. The cake was then washed with hexane (250 mL) to give a light yellow crystalline solid; 116.0 g. GC showed 86.5% product with some residual low boiling point components. The yellow filtrate was concentrated on a rotary evaporator at 35° C. to give a yellow viscous oil; 39.2 g. GC showed mostly low boiling point components with some residual product (17.7%).

The solid was stirred magnetically at room temperature in a mixture of hexane (250 mL) and diethyl ether (50 mL) for 45 min. The slurry was suction filtered and washed with hexane to give a white, crystalline solid; 82.85 g. mp=83-85° C. $^1$H-NMR and $^{13}$C-NMR were consistent with the desired alcohol. GC showed only the desired alcohol.

The ether-hexane filtrate was concentrated on a rotary evaporator at 35° C. to give a yellow slush; 33.0 g. GC showed impure alcohol (69%). Each filtrate was slurried in hexane (100 mL) and ether (25 mL) to give white solid. The samples were stoppered and allowed to stand at room temperature. The two slurries were suction filtered into the same Buchner funnel and rinsed with 4:1 hexane:ether (50 mL) to give a white solid; 3.0 g. mp=82-85° C. $^1$H-NMR showed the desired alcohol with a slightly higher level of impurities. GC showed 99% of the desired alcohol. This solid was combined with the first crop. Total yield=85.85 g (54.8% yield).

$^1$H-NMR (CDCl$_3$, ppm): 7.6 (Ar 1H); 7.5 (Ar 1H); 7.2-7.4 (Ar 5H); 6.9 (Ar 1H); 6.05 (OH); 3.82 (OCH$_3$); 2.75 & 2.74 (d J=4.7 Hz, CH).

Example 3

(2-Methoxy-5-trifluoromethylphenyl)-phenyl methanone

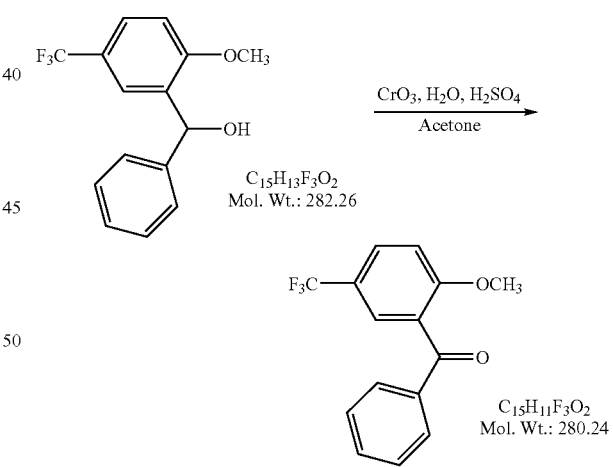

Preparation of Jones' Reagent: Chromium trioxide (23.5 g; 0.235 mol) was dissolved in 47 mL deionized water and cooled in an ice bath. Concentrated sulfuric acid (19.7 mL; 0.37 mol) was added dropwise over 15 min at 5-15° C. Additional water (18 mL) was added to dissolve the precipitated solids and transfer the red solution to the addition funnel.

Oxidation: In a 1000 mL, 4-neck flask, a mechanically stirred solution of (2-methoxy-5-trifluoromethyl-phenyl) phenyl methanol (85.6 g; 0.303 mol) in 650 mL of acetone was cooled in a water bath to 20° C. The Jones' reagent was added dropwise over a period of 49 min. The temperature was kept in the range of 20-25° C. At the end of the addition, the green solids clumped on the bottom of the flask. An aliquot (5 drops) of the light orange mother liquor was partitioned between ether (1 mL) and 10% aq NaHCO$_3$ (0.5 mL). The dried (Na$_2$SO$_4$) ether layer was analyzed. TLC (thin layer chromatography) showed the desired ketone with no detectable starting alcohol. After 25 min, the stirred slurry was treated with isopropanol (15 mL; 0.196 mol) in one portion to destroy the excess oxidant. After another 15 min, solid sodium bicarbonate (62.3 g; 0.742 mol) was added portionwise over 5 min. The mother liquor was then decanted away from the blue-green tarry solid through a pad of prewetted Celite 545 (30 g). The blue-green tar was washed with acetone (3×100 mL). The light yellow filtrate was concentrated on a rotary evaporator at 40° C. to give a two-phase light yellow oily water mixture. This material was dissolved in ether (1000 mL) and washed successively with 10% aqueous NaHCO$_3$ (400 mL) and then saturated brine (400 mL).

The ether layer was dried over MgSO$_4$, filtered and concentrated on a rotary evaporator at 45° C. to give a pale yellow oil; 83.95 g. This oil was evaporated further on a Kugelrohr at 50° C. and 0.15-0.4 torr for 30 min; 83.55 g. GC indicated 99.7% of the desired ketone. $^1$H-NMR showed the desired ketone with some detectable impurities. $^{13}$C-NMR was similar to the previous spectrum with some detectable impurities. The yield was 98.3%.

$^1$H-NMR (CDCl$_3$, ppm): 7.8-7.4 (Aromatic 7H); 7.05 (Aromatic 1H); 3.77 (OCH$_3$).

Example 4

N,N-diisopropyl bromoacetamide

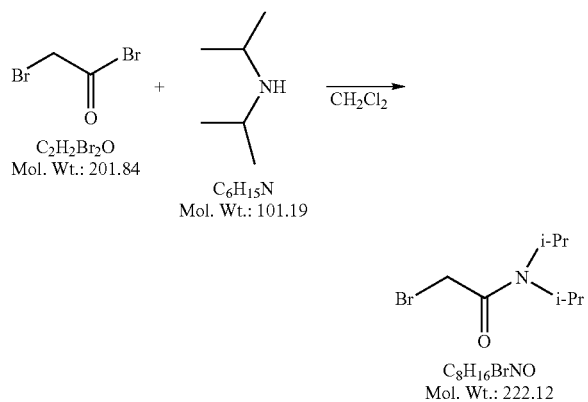

Under a nitrogen atmosphere, a mechanically stirred solution of bromoacetyl bromide (103.65 g; 0.51 mol, Aldrich) in 375 mL anhydrous dichloromethane was cooled in an ice bath. A solution of diisopropylamine (130 mL; 0.93 mol, Aldrich) in 125 mL anhydrous dichloromethane was added dropwise over a period of 92 min at 4-11° C. The yellow slurry was stirred in the ice bath for 46 min. The resulting grayish slurry was suction filtered and washed with a minimal amount of dichloromethane to give a white solid.

The amber-green filtrate was washed successively with ice-water (4×200 mL), 10% aqueous NaHCO$_3$ (200 mL) and saturated brine (200 mL). The red amber layer was dried over Na$_2$SO$_4$, filtered and concentrated on a rotary evaporator at 45° C. to give a red oil; 97.15 g. GC showed one major component (94.6%) and two minor impurities. MS showed that the major volatile component was the desired product, giving a weak but detectable M$^+$ ion at 222 and 224 m/z.

This oil was dissolved in 100 mL hexane and cooled in the freezer at −30° C. for 70 min. Trituration of the solution with a glass rod gave immediate precipitation. The resulting solidified mass was diluted with hexane (100 mL) the mass broken up, suction filtered and washed with a minimal amount of hexane to give a tan solid; 73.45 g.

Uncorrected mp=59-61° C.; lit mp=64-65.5° C. $^1$H-NMR and $^{13}$C-NMR were consistent with the desired amide. GC showed 97.5% of the desired product. The yield was 64.3%.

$^1$H-NMR (CDCl$_3$, ppm): 4.0 (1Ha); 3.85 (2H); 3.45 (1Hb); 1.43 & 1.41 (6H); 1.30 & 1.28 (6H).

Example 5

Diethyl N,N-diisopropylaminocarbonylmethyl phosphonate

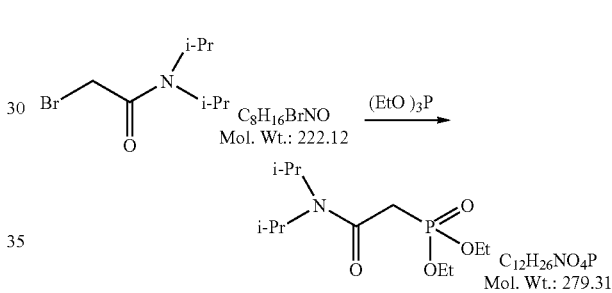

A 250 mL 3-neck flask was equipped with a Teflon-coated thermocouple, a distillation head and a 60 mL addition funnel. N,N-Diisopropyl bromoacetamide (67.9 g; 0.306 mol) was charged to the flask and heated with a heating mantle. After the solid melted, the brown oil was stirred magnetically and heated to 110° C. under a nitrogen atmosphere. Neat triethyl phosphite (57 mL; 0.332 mol, Aldrich) was added dropwise over a period of 30 min at 104-117° C., as bromoethane co-product was distilled off at 35-45° C. and collected in a 100 mL flask.

At the end of the addition, the red amber oil was heated at 110° C. under nitrogen for 3 h. Amount of distillate=25.5 g. GC of an aliquot (1 drop) in ether (0.5 mL) showed the desired product with no detectable starting bromide. The red amber oil was transferred to a 500 mL flask with some ether and stripped on a rotary evaporator at 45° C.; 88.3 g. This red amber oil was then stripped on a Kugelrohr at 75° C. and 0.15-0.4 torr for 1 h to remove the residual low boiling impurities and leave a red amber oil; 78.3 g. GC showed 94% product with negligible low boiling point components. $^1$H-NMR was consistent with the desired product, showing two different isopropyl groups. $^{13}$C-NMR was also consistent with the desired diethyl phosphonate. The yield was 91.6%.

$^1$H NMR (CDCl$_3$, ppm): 4.07-4.25 (5H); 3.45 (1H); 3.07 & 2.99 (2H); 1.3-1.45(12H); 1.18-1.25 (6H).

Example 6

N,N-Diisopropyl-3-(2-methoxy-5-trifluoromethylphenyl)-3-phenylpropenamide (isomeric mixture)

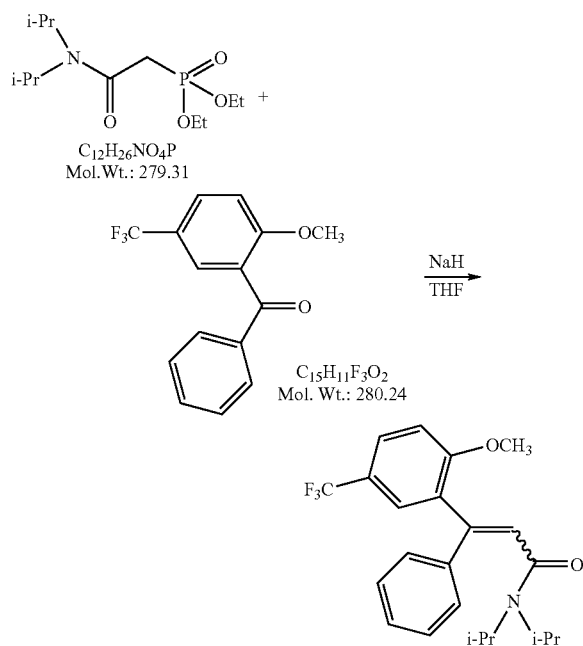

All glassware was dried in an oven overnight at 105° C. and assembled hot under nitrogen. In a 3-neck 1000 mL flask, 95% sodium hydride (7.8 g; 0.309 mol) was slurried in anhydrous tetrahydrofuran (70 mL) under nitrogen with magnetic stirring. A solution of diethyl N,N-diisopropylamino-carbonylmethyl phosphonate (79.65 g; 0.285 mol) in 125 mL anhydrous THF was added dropwise over 83 min at 24-27° C. The addition funnel was rinsed with 20 mL anhydrous THF into the reactor. After stirring the resulting amber solution for 19 min at ambient temperature under nitrogen, a solution of (2-methoxy-5-trifluoromethylphenyl) phenyl methanone (83.55 g; 0.298 mol) in 125 mL anhydrous THF was added dropwise over 108 min. The mild exothermic reaction raised the temperature from 23 to 27° C. during this addition. The addition funnel was rinsed with 20 mL anhydrous THF into the reactor. After stirring at ambient temperature for 38 min, the red amber solution was heated at 55° C. using a heating mantle.

After 17 h at 55° C., heating was stopped. An aliquot (5 drops) of the red amber solution was partitioned between ether (1 mL) and water (0.5 mL). GC showed the two isomeric products in a ratio of 57:43 with significant amount of ketone due to overcharge thereof. Water (300 mL) was added to the brown amber solution with no obvious reaction and the mixture was extracted with ether (1000 mL and 500 mL). The combined ether layers were washed with saturated brine (2×200 mL), dried over $MgSO_4$ and then suction filtered. GC gave similar results as the aliquot. The brown amber filtrate was concentrated on a rotary evaporator at 45° C. to give a brown oil; 118.05 g. This oil was distilled in a Kugelrohr at 144-146° C. and 0.3 torr to give a light yellow distillate (45.2 g) and a dark brown tar (68.15 g). TLC and GC showed only partial separation of the ketone from desired olefins in the pot residue. The distillate, which contained mostly ketone, was also contaminated with the desired olefins.

The brown tar from the pot residue was dissolved in 120 mL 3:1 hexane:ethyl acetate while warming with a heat gun. Upon standing overnight at room temperature, a crystalline solid formed. This solid was filtered off and washed with hexane to remove the amber color and leave colorless plates; 17.2 g. mp=110-112° C. GC showed only the major olefinic product. $^1$H-NMR and $^{13}$C-NMR showed a single olefinic isomer.

The amber filtrate was concentrated on a rotary evaporator at 45° C. to give a brown tar; 53.65 g. This material was dissolved in 3:1 hexane:ethyl acetate (100 mL) by warming with a heat gun. This solution was introduced to a prewetted Biotage 75L silica gel column with a radial compression of $1.4 \times 10^5$ N/m² (20 psi) and a solvent pressure of $2.5 \times 10^5$ N/m² (36 psi). The sample was rinsed and chased onto the column with 4:1 hexane:ethyl acetate (2×50 mL). The column was then eluted with a mixture of 10 000 mL hexane and 2000 mL ethyl acetate, and then with a mixture of 4000 mL hexane and 1000 mL ethyl acetate. After collecting a void volume of 1000 mL, including pre-wet and sample introduction, fractions of 425 mL were collected and analyzed by TLC for composition. TLC showed some impure ketone and mixed olefins; 28.85 g. Fractions containing the two desired olefins were combined and concentrated on a rotary evaporator. Total yield=17.2+28.85=46.05 g (39.9% yield based on phosphonate).

Analysis (Free Base 1:1 mix of olefins A and B): $^1$H NMR (CDCl$_3$, ppm): 7.6 (Aromatic 1H); 7.45 (Aromatic 1H); 7.3 (Aromatic 5H); 6.95 (Aromatic 1H); 6.6 & 6.2 (olefin singlets A & B, 1H); 4.2-4.4 (1H); 3.75 & 3.70 (OMe singlets A & B, 1H); 3.3 (1H); 3.4 (1H); 1.42 (doublet B Me); 1.28 (doublet A Me), 1.09 (doublet A Me); 0.84 (doublet B Me).

Example 7

N,N-Diisopropyl-3-(2-methoxy-5-trifluoromethylphenyl)-3-phenylpropanamide

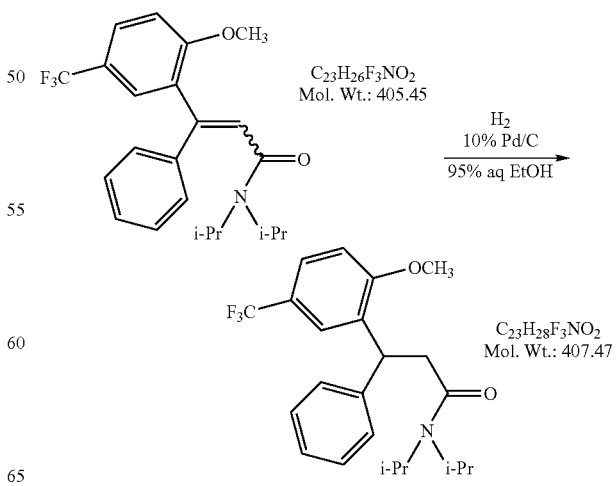

In a 1000 mL Parr bottle, an isomeric mixture of N,N-diisopropyl-3-(2-methoxy-5-trifluoromethylphenyl)-3-phenylpropenamide (46.05 g; 113.6 mmol) was dissolved in 500 mL 95% aqueous ethanol. 10% Palladium on carbon catalyst (2.0 g) was pressurized and vented five times with hydrogen gas at $2.1 \times 10^5$ to $2.8 \times 10^5$ N/m² (30-40 psi). The bottle was then pressurized to $2.7 \times 10^5$ N/m² (38.5 psi) and shaken at ambient temperature. After 3 h, the pressure drop appeared to stop at $4.8 \times 10^4$ N/m² (7 psi). An aliquot (5 drops) was filtered through a small plug of Celite and washed with reagent alcohol (0.5 mL). GC showed about 82% conversion, with the remainder being the less abundant olefin. The reaction mixture was repressurized on the Parr shaker at $2.8 \times 10^5$ N/m² (40.5 psi).

After another 20 h (23 h total), the hydrogen pressure dropped another $6.9 \times 10^3$ N/m² (1 psi). GC of an aliquot worked up as above showed product with no detectable starting olefins. The catalyst was suction filtered through a pad of Celite in a Buchner funnel and washed with reagent alcohol (200 mL). Gravity filtration of a portion of the black filtrate through fluted paper removed only a small amount of catalyst. Another filtration through a smaller pad of Celite in a Buchner funnel removed only a small amount of catalyst after washing with ethanol (100 mL). The gray filtrate was then washed through a plug of silica gel (10-15 g) and washed with ethanol (100 mL) to give a still gray filtrate. This filtrate was concentrated on a rotary evaporator at 45° C. to give a light gray solid; 58.35 g.

This solid was dissolved in chloroform (300 mL) and the catalyst coagulated on the bottom of the flask. The catalyst was then suction filtered off through a small pad of Celite in Buchner funnel and washed with chloroform (100 mL). The faint yellow filtrate was concentrated on a rotary evaporator at 45° C. to give a white solid; 49.35 g. This solid was transferred to a bottle and dried in the vacuum oven at 50° C. for 110 min until constant weight; 44.6 g (96.4% yield). mp=92-94° C. ¹H-NMR and ¹³C-NMR matched the desired saturated amide.

¹H NMR (CDCl₃, ppm): 7.45 (Aromatic 2H); 7.2 (Aromatic 5H); 6.85 (Aromatic 1H); 5.05 (PhCH, 1H); 4.05 (1H); 3.8 (OCH₃); 3.4 (1H); 3.0 (2H); 1.05-1.35 (12H).

¹³C NMR (CDCl₃, ppm): 169.6; 159.8; 143.8; 133.6; 128.3; 128.1; 126.3; 125.0; 124.9; 124.6; 110.8; 55.7; 48.7; 46.0; 41.1; 39.9; 21.0, 20.8, 20.6.

Example 8

N,N-Diisopropyl-3-(2-methoxy-5-trifluoromethylphenyl)-3-phenylpropanamine

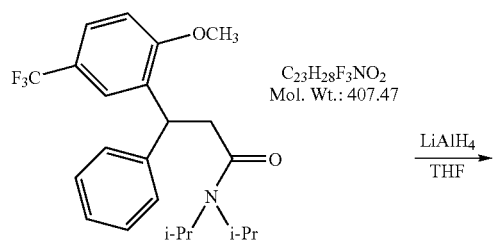

C₂₃H₂₈F₃NO₂
Mol. Wt.: 407.47

LiAlH₄ / THF →

-continued

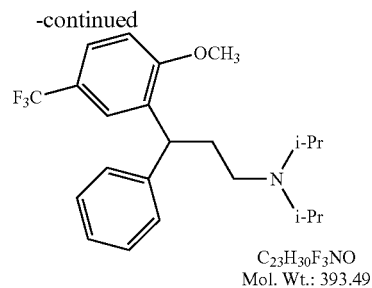

C₂₃H₃₀F₃NO
Mol. Wt.: 393.49

Solid N,N-diisopropyl-3-(2-methoxy-5-trifluoromethylphenyl)-3-phenylpropanamide (41.9 g; 102.8 mmol) was added to a 1000 mL single neck flask and chased with anhydrous tetrahydrofuran (10+5 mL). The flask was equipped with a Claisen head, connected to a reflux condenser to a nitrogen bubbler. Through a septum on the Claisen head was inserted a Teflon-coated thermocouple. 1M Lithium aluminum hydride in THF (400 mL; 400 mmol) was cannulated into the flask under nitrogen using a 100 mL graduated cylinder with a septum. The magnetically stirred solution was heated to reflux under nitrogen. The red solution was heated at reflux for 4 h.

After cooling to room temperature overnight, an aliquot (5 drops) was quenched in ether (0.5 mL) and water (0.5 mL). The mixture was extracted with ethyl acetate (0.5 mL) and dried over Na₂SO₄. GC showed ≈12:1 of product:starting amide with only trace amounts of norfluoroamine. The amber solution was heated to reflux again and held at reflux. After another 2 h at reflux (6 h total) GC of an aliquot worked up as above showed a 50:41 mixture of product:starting amide. The yellow-orange solution was heated at reflux again for another 2 h (8 h total). GC of an aliquot worked up as above showed a 52:39 mixture of product:starting amide.

The yellow solution was cooled in an ice bath. Water (15 mL) was added dropwise from a 20 mL plastic syringe over 68 min at 8-15° C. 15% aqueous NaOH (15 mL) was then added dropwise at 10-17° C. over 36 min. Water (45 mL) was added dropwise over 39 min at 12-25° C. The slurry was stirred overnight as the ice bath equilibrated to room temperature.

The slurry was suction filtered and the salts washed with ethyl acetate (600 mL). The light yellow filtrate was washed with saturated brine (2×300 mL) and dried over Na₂SO₄. After filtering off the drying agent, the light yellow filtrate was concentrated on a rotary evaporator at 45° C. to give a yellow viscous oil; 41.2 g. GC showed a 2:1 relation of product:starting amide with residual difluoro- and norfluoro-impurities. This oil was dissolved in chloroform (40 mL).

This solution was added to a pre-wetted Biotage 75M silica gel column with a radial compression of $2.8 \times 10^5$ N/m² (40 psi) and a solvent pressure of $1.4 \times 10^5$ N/m² (20 psi). The sample was chased and rinsed onto the column with additional chloroform (2×25 mL). The column was then eluted with 8000 mL chloroform mixed with 80 mL reagent alcohol, and then with 4000 mL chloroform mixed with 445 mL reagent alcohol. After collecting a void volume of 500 mL, including column pre-wet and sample introduction, fractions of 425 mL were collected and analyzed by TLC. Selected samples were also analyzed by GC. Based on this information, fractions containing common components were combined, concentrated on a rotary evaporator at 45° C. and then on a Kugelrohr at 25-50° C. and <0.5 torr to give the following results:

Fractions 7-8: GC showed 91% desired amine contaminated with amide (5%), difluoro impurity (1.3%) and norfluoro impurity (1.6%). Yield based on 91% assay=16.4%.

Fractions 9-23: Off-white solid; 15.25 g; $^1$H-NMR showed the desired amine with some residual ethanol. GC showed 98% desired amine with 2% difluoro impurity. The solid was dried further on a Kugelrohr at 50° C. and 0.2 torr for 1 h; 14.65 g (36.3% yield). $^1$H-NMR showed negligible ethanol and only desired amine. mp=61-63° C.

Fractions 24-28: GC showed 83% desired amine and 16% difluoro impurity.

$^1$H NMR (CDCl$_3$, ppm): 7.5 (1H); 7.4 (1H); 7.3 (4H); 7.2 (1H); 6.8 (1H); 6.9 (1H); 4.4 (PhCH, 1H); 3.8 (3H, OMe); 3.0 (2H); 2.4 (2H); 2.2 (2H); 1.0 (12H).

Example 9

N,N-Diisopropyl-3-(2-hydroxy-5-trifluoromethylphenyl)-3-phenylpropanamine

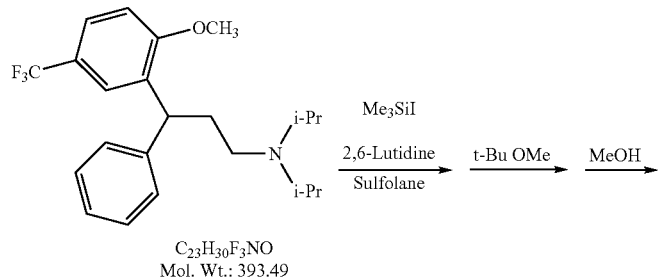

A magnetically stirred slurry of N,N-diisopropyl-3-(2-methoxy-5-trifluoromethyl-phenyl)-3-phenylpropanamine (1.0 g; 2.54 mmol) in 1.5 mL sulfolane and 2,6-lutidine (0.3 mL; 2.58 mmol) was treated with trimethylsilyl iodide (1.0 mL; 7.03 mmol) in one portion with no evidence of additional precipitation. This slurry was heated at 92-103° C. under nitrogen to give a yellow solution.

After heating at 92-103° C. for 20 h, an aliquot (1 drop) was taken, mixed with 0.1 mL tert-butyl methyl ether and then diluted with 24 mL 50% aqueous acetonitrile containing 0.05% formic acid. Liquid chromatography (LC) showed 48% conversion to the phenol and the trimethylsilylated phenol. The red solution was heated again at 93-102° C. under nitrogen. LC of an aliquot worked up as above showed 69.1% conversion to the phenol and the trimethylsilylated phenol.

After a total of nearly 6 days at 93-102° C., LC showed about 93% conversion to the phenol and the trimethylsilylated phenol.

Electrospray MS (Positive ion) MH$^+$=m/z 380.

$^1$H NMR (CDCl$_3$, ppm): 7.3 (Aromatic 7H); 6.9 (Aromatic 2H); 4.5 (1H); 3.3 (2H); 2.8 (1H); 2.4 (2H); 1.3 (12H). $^{13}$C NMR (CDCl$_3$, ppm): 159.5; 143.6; 133.0; 128.5; 128.4; 126.6; 125.5; 125.4; 124.5; 118.5; 48.4 (iPrCH); 42.4 (CH$_2$N); 39.8 (PhCH); 33.4 (CH$_2$); 19.6 (iPr CH$_3$).

Example 10

Tartrate Salt (1:1) of N,N-Diisopropyl-3-(2-hydroxy-5-trifluoromethyl-phenyl)-3-phenylpropanamine

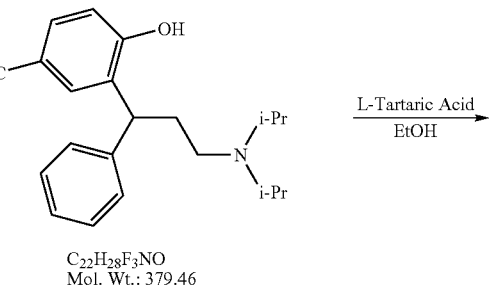

-continued

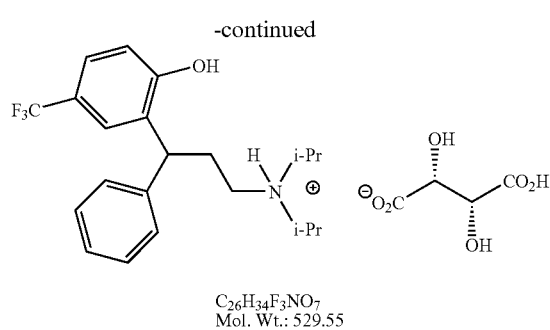

A magnetically stirred solution of N,N-diisopropyl-3-(2-hydroxy-5-trifluoromethyl-phenyl)-3-phenylpropanamine (326.5 mg; 0.86 mmol) in 4 mL anhydrous ethanol was treated with solid L-tartaric acid (135 mg; 0.90 mmol) and chased with 1 mL anhydrous ethanol. The resulting solution was heated at reflux for 1 h. The brown solution was cooled in an ice bath with no evidence of precipitation. The cold brown solution was concentrated on a rotary evaporator at 50° C. to give a gold, creeping foam; 461.4 mg. This foam was slurried in ether (5 mL), suction filtered and washed with ether to give a gold solid that became tacky almost immediately on the filter. This hygroscopic solid was dissolved in methanol (10 mL) and concentrated on a rotary evaporator at 25-50° C. to approximately 2 mL volume. Addition of ether (≈5 mL) until turbid gave precipitation of a brown oil. The mixture was concentrated again to give a gold foam; 451.5 mg. This foam was broken up with a spatula and dried in a vacuum oven overnight at 45° C.

Amount of brown-gold glass=436.4 mg. Insoluble in $CDCl_3$. LC showed the desired amino-phenol with a M−1 ion at 378 m/z and tartaric acid with a M−1 ion at 149 m/z by electrospray in the negative ion mode. $^1$H-NMR was consistent with the 1:1 tartrate salt with the appropriate downfield shifts of the various aliphatic proton signals. $^{13}$C-NMR showed the two unique carbons of tartaric acid and all carbons of the phenolic amine except for missing two quaternary aromatic carbons and the trifluoromethyl carbon.

Electrospray MS (negative ion) M−1=m/z 378 (base); M−1=149 (tartrate).

$^1$H NMR ($CD_3OD$, ppm): 7.3 (Aromatic 7H); 6.9 (Aromatic 1H); 4.0 (3H); 3.6 (2H); 3.0 (2H); 2.5 (2H); 1.3 (12H). $^{13}$C NMR ($CD_3OD$, ppm): 176.5 (tartrate $CO_2H$); 159.1; 143.03; 129.7; 129.2; 127.9; 126.1; 126.1; 116.5; 73.8 (tartrate CH); 56.4 (iPrCH); 47.6 ($CH_2N$); 43.2 (PhCH); 33.2 ($CH_2$); 18.0 (iPr $CH_3$).

Example 11

In vitro muscarinic receptor binding assay of N,N-Diisopropyl-3-(2-hydroxy-5-trifluoromethylphenyl)-3-phenylpropanamine Affinities of test compounds for muscarinic receptor subtypes $M_1$-$M_4$ were determined. Competition radioligand binding experiments employed 11 drug concentrations run in duplicate. [$^3$H]N-methylscopolamine (NMS) was used as an antagonist radioligand, at the concentration equal to its equilibrium dissociation constant ($K_d$) for each receptor subtype. Nonspecific binding (90-95% of total) was defined with cold atropine added in excess (5 μM). Total binding was determined with phosphate buffered saline (PBS). Cloned human receptors permanently expressed in CHO cells were the source of all binding sites. Membranes were purchased from Receptor Biology division of Perkin Elmer Life Sciences (Beltsville, Md.). The assays were run in scintillation proximity assay (SPA) format. Binding mixtures were made in flexible, 96-well, Wallac Micro-Beta plates by the addition of 11 μl of drug dilution, 11 μl of radioligand, and 178 μl of membrane/SPA bead suspension (100 mg of WGA-coated SPA beads, incubated with 5-15 μg protein/plate in 10 ml PBS for 30 min at room temperature, followed by low-speed centrifugation and resuspension in 2 ml PBS). After sealing and incubation at room temperature for 1 hour the plates were counted in a Wallac Micro-Beta scintillation counter. $IC_{50}$ values were estimated by fitting the data to a one-site competition model:

$$Y = T/(1+10^{log(X)-log(IC50)}),$$

where Y is the specific CPM's bound at concentration X, and T is the specific CPM's bound in the absence of competitor. Inhibition constants ($K_i$) were calculated using the Cheng-Prushoff equation (Cheng, Y; Prushoff, W H, Biochem Pharmacol 22: 3099-3108, 1973). Curve fitting and $K_i$ calculations were carried out using GraphPad Prism, version 3.0 (San Diego, Calif.). The results are displayed in the following Table 1.

TABLE 1

| COMPOUND | $M_1$ $K_i$ (nM) | $M_2$ $K_i$ (nM) | $M_3$ $K_i$ (nM) | $M_4$ $K_i$ (nM) |
|---|---|---|---|---|
| N,N-Diisopropyl-3-(2-hydroxy-5-trifluoromethyl-phenyl)-3-phenylpropanamine (Racemic) | 3.9 | 8.4 | 16 | 6.0 |
| tolterodine (R(+)enantiomer) | 0.79 | 1.7 | 1.7 | 0.64 |

Results are the average of four separate determinations.

In Vitro Binding

Tolterodine tartrate (the R(+) enantiomer) and racemic N,N-diisopropyl-3-(2-hydroxy-5-trifluoromethylphenyl)-3-phenylpropanamine according to the invention and example 9 were tested. Since the S (−) enantiomer of tolterodine has relatively less affinity for muscarinic receptors, the activity of N,N-diisopropyl-3-(2-hydroxy-5-trifluoromethylphenyl)-3-phenylpropanamine is presumed to reside primarily with the R(+) enantiomer, and measured $K_i$'s for the R(+) enantiomer of N,N-diisopropyl-3-(2-hydroxy-5-trifluoromethylphenyl)-3-phenylpropanamine are predicted to be about half of the values in the table. Both compounds showed potent affinity (low to sub-nanomolar $K_i$'s) for four muscarinic receptor subtypes. As a competitive muscarinic antagonist, tolterodine is regarded as having low muscarinic receptor subtype selectivity, but a favorable ratio of activity at bladder receptors, relative to salivary gland receptors (Nilvebrant et al, Neurourol Urodyn 15: 310-311 (1996)).

N,N-diisopropyl-3-(2-hydroxy-5-trifluoromethylphenyl)-3-phenylpropanamine is relatively less potent at the m3 receptor. Gillberg et al, Eur J Pharmacol 349(2-3): 285-292 (1998) have suggested that decreased potency at the m3 receptor may improve the ratio of desired effects at the bladder, relative to effects on the salivary glands that result in dry mouth. Thus, the compounds according to the invention may be helpful in exhibiting functional selectivity for antimuscarinic effects on urinary bladder over salivary glands in vivo, since a selectivity for muscarinic M3/m3 over M2/m2 receptors may result in a more pronounced effect on salivation than on bladder contraction.

Example 12

Preparation of Other Compounds According to the Invention

Using the general procedure described in examples 1-10, other compounds according to the invention are readily synthesized employing appropriate starting compounds. The choice of starting compounds can be made by the skilled man using the information above.

In particular, the 5-trifluoromethyl group is interchangeable to any of the corresponding groups in that position according to invention, including trihalomethyl and mono- or dihalomethyl, optionally substituted with $C_1$-$C_4$ alkyl. The $C_1$-$C_4$ alkyl is optionally substituted with halogen.

Example 13

Protection from CYP2D6 metabolism

[$^{14}$C]-labeled N,N-diisopropyl-3-(2-hydroxy-5-trifluoromethylphenyl)-3-phenylpropanamine is synthesized, following the general procedure of examples 1-9. Approximately 10 μM of the compound is incubated with microsomes containing P450 CYP2D6 enzyme (20 pmol) in 100 mM potassium phosphate buffer (pH 7.4) and 1 mM P-NADPH at 37° C. in a final volume of 250 μl for 20 min.

The incubations are analyzed for the parent drug and its metabolites by HPLC using standard procedures. The amount of each metabolite is calculated from the resulting radiochromatogram. The retention times of formed metabolites are compared with the retention times of synthesized reference standards, and the identity of the formed metabolites is further confirmed by electrospray ionization mass spectrometry. The compound according to the invention is not readily hydroxylated at the 5-trifluoromethyl substituent.

Thus, the 3,3-diphenylpropylamines according to the invention do not possess a high propensity for being oxidized by the P450 CYP2D6 enzyme. Oxidation of 3,3-diphenylpropylamines, such as tolterodine, is generally held to be an important factor in pharmacokinetic differences between poor and extensive metabolizers, resulting in intersubject pharmacokinetic variability.

The invention claimed is:

1. N,N-diisopropyl-3-(2-hydroxy-5-trifluoromethylphenyl)-3phenylpropanamine tartrate.

2. A pharmaceutical composition comprising N,N-diisopropyl-3-(2-hydroxy-5-trifluoromethylphenyl)-3-phenylpropanamine, or a pharmaceutically acceptable salt thereof, and a suitable pharmaceutical carrier therefor.

3. The pharmaceutical composition of claim 2, wherein said pharmaceutically acceptable salt of N,N-diisopropyl-3-(2-hydroxy-5-trifluoromethylphenyl)-3-phenylpropanamine is the tartrate salt.

4. A method of treating urinary disorders in a mammal, including man, comprising administering to said mammal, in need of such a treatment, a therapeutically effective amount of N,N-diisopropyl-3-(2-hydroxy-5-trifluoromethylphenyl)-3-phenylpropanamine, or a pharmaceutically acceptable salt thereof, or a therapeutically effective amount of a pharmaceutical formulation comprising said compound or said pharmaceutically acceptable salt thereof.

5. The method of claim 4, wherein said pharmaceutically acceptable salt of N,N-diisopropyl-3-(2-hydroxy-5-trifluoromethylphenyl)-3-phenylpropanamine is the tartrate salt.

* * * * *